(12) United States Patent
Brisken

(10) Patent No.: US 6,228,046 B1
(45) Date of Patent: *May 8, 2001

(54) CATHETERS COMPRISING A PLURALITY OF OSCILLATORS AND METHODS FOR THEIR USE

(75) Inventor: Axel F. Brisken, Fremont, CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/033,834

(22) Filed: Mar. 3, 1998

Related U.S. Application Data (63) Continuation-in-part of application No. 08/867,007, filed on Jun. 2, 1997, now Pat. No. 5,931,805.

(51) Int. Cl.[7] ............................. A61B 17/20; A61B 17/32
(52) U.S. Cl. .............................................. 604/22; 606/169
(58) Field of Search ....................... 604/19, 22; 606/169, 606/171; 600/466, 467, 471

(56) References Cited

U.S. PATENT DOCUMENTS

| | | |
|---|---|---|
| 3,433,226 | 3/1969 | Boyd . |
| 3,565,062 | 2/1971 | Kuris . |
| 4,692,139 | 9/1987 | Stiles . |
| 4,698,058 | 10/1987 | Greenfeld et al. . |
| 4,808,153 | 2/1989 | Parisi ..................................... 604/22 |
| 4,870,953 | 10/1989 | DonMicheal et al. . |
| 4,919,647 | 4/1990 | Nash . |
| 4,936,281 | 6/1990 | Stasz . |
| 4,948,587 | 8/1990 | Kost et al. . |
| 5,053,044 | 10/1991 | Mueller et al. . |
| 5,069,664 | 12/1991 | Guess et al. . |
| 5,085,662 | 2/1992 | Willard . |
| 5,117,831 | 6/1992 | Jang et al. . |
| 5,163,421 | 11/1992 | Bernstein et al. . |
| 5,181,920 | 1/1993 | Mueller et al. . |
| 5,197,946 | 3/1993 | Tachibana . |

(List continued on next page.)

FOREIGN PATENT DOCUMENTS

| | | | |
|---|---|---|---|
| 0189329A2 | 7/1989 | (EP) . | |
| 3-63041 | 3/1991 | (JP) . | |
| WO 90/01300 | 2/1990 | (WO) . | |
| WO 91/19529 | 12/1991 | (WO) . | |
| WO 94/05361 | 3/1994 | (WO) . | |
| WO 95/22284 | 8/1995 | (WO) | ............................. A61B/08/12 |
| WO 95/24159 | 9/1995 | (WO) | ............................. A61B/17/36 |
| WO 96/29935 | 10/1996 | (WO) | ............................. A61B/8/12 |

OTHER PUBLICATIONS

Tachibana, M.D., Katsuro "Enhancement of Fibrinolysis with Ultrasound Energy," *JVIR*, vol. 3, No. 2, 1992, pp. 299–303.

Yumita et al. "Synergistic Effect of Ultrasound and Hematoporphyrin on Sarcoma 180," *Jpn. J. Cancer Res.*, vol. 81, 1990, pp. 304–308.

(List continued on next page.)

*Primary Examiner*—Sharon Kennedy
*Assistant Examiner*—Michael J. Hayes
(74) *Attorney, Agent, or Firm*—Townsend and Townsend and Crew LLP (57) ABSTRACT

A catheter comprises a catheter body having a vibrational transducer disposed at or near its distal end. The vibrational transducer comprises a plurality of oscillators such as bending plate oscillators or other conventional oscillators each having a vibrational surface capable of imparting pressure waves. The plurality of oscillators may be disposed at a distal end of the catheter body or may alternatively be disposed within the catheter body. The catheter may further comprise lumens for drug delivery, balloons for encircling the transducer structures, or the like. The catheters are useful in a variety of lumenal therapeutic procedures, including drug delivery, stenotic disruption within blood vessel, and the like.

20 Claims, 11 Drawing Sheets

U.S. PATENT DOCUMENTS

| | | |
|---|---|---|
| 5,267,954 | 12/1993 | Nita . |
| 5,267,985 | 12/1993 | Shimada et al. . |
| 5,269,297 | 12/1993 | Weng et al. . |
| 5,276,546 | 1/1994 | Mische et al. . |
| 5,282,785 | 2/1994 | Shapland et al. . |
| 5,286,254 | 2/1994 | Shapland et al. . |
| 5,304,115 | 4/1994 | Pflueger et al. . |
| 5,315,998 | 5/1994 | Tachibana et al. . |
| 5,318,014 | 6/1994 | Carter . |
| 5,324,255 | 6/1994 | Passafaro et al. . |
| 5,342,292 | 8/1994 | Nita et al. . |
| 5,344,395 | 9/1994 | Whalen et al. . |
| 5,362,309 | 11/1994 | Carter . |
| 5,380,273 | 1/1995 | Dubrul et al. . |
| 5,397,301 | 3/1995 | Pflueger et al. . |
| 5,447,509 | 9/1995 | Mills et al. ............................. 606/1 |
| 5,456,259 | 10/1995 | Barlow et al. .................. 128/662.03 |
| 5,458,568 | 10/1995 | Racchini et al. ....................... 604/19 |
| 5,458,631 | 10/1995 | Xavier ................................. 607/117 |
| 5,462,523 | 10/1995 | Samson et al. ........................ 604/30 |
| 5,465,725 | 11/1995 | Seyed-Bolorforosh ......... 128/662.03 |
| 5,474,530 | 12/1995 | Passafaro et al. ..................... 604/22 |
| 5,474,531 | 12/1995 | Carter ................................... 604/22 |
| 5,620,479 | 4/1997 | Diederich .............................. 607/97 |
| 5,735,811 * | 4/1998 | Brisken ................................. 604/22 |
| 5,931,805 * | 8/1999 | Brisken ................................. 604/22 |

OTHER PUBLICATIONS

Rosenschein, M.D., Uri et al. "Experimental Ultrasonic Angioplasty: Disruption of Atherosclerotic Plaques and Thrombi in Vitro and Arterial Recanalization in Vivo," *JACC*, vol. 15, No. 3, Mar. 1, 1990, pp. 711–717.

* cited by examiner

CATHETERS COMPRISING A PLURALITY OF OSCILLATORS AND METHODS FOR THEIR USE

CROSS-REFERENCE TO RELATED APPLICATIONS

This application is a continuation-in-part of, and claims the benefit of priority from, commonly-assigned, co-pending U.S. patent application Ser. No. 08/867,007, filed Jun. 2, 1997, now U.S. Pat. No. 5,931,805. The complete disclosure of this application is hereby incorporated herein by reference.

BACKGROUND OF THE INVENTION

1. Field of the Invention

The present invention relates generally to medical devices and methods. More particularly, the present invention relates to apparatus and methods for performing intralumenal procedures using catheters which can impart vibratory energy to a blood vessel or other body lumens being treated.

Despite the growing sophistication of medical technology, vascular (blood vessel) diseases, such as acute myocardial infarction (heart attack) and peripheral arterial thrombosis (blood clots in leg arteries), remain a frequent, costly, and very serious problem in health care. Current methods of treatment, often expensive, are not always effective. In the U.S. alone, the cost of treatment and support and the loss of productivity due to vascular diseases together exceed $40 billion per year.

The core of the problem is that diseased sites within the blood vessels narrow and eventually become completely blocked as a result of the deposition of fatty materials, cellular debris, calcium, and/or blood clots, thereby blocking the vital flow of blood. Current treatments include drugs, interventional devices, and/or bypass surgery. High doses of thrombolytics (clot-dissolving drugs) are frequently used in an effort to dissolve the blood clots. Even with such aggressive therapy, thrombolytics fail to restore blood flow in the affected vessel in about 30% of patients. In addition, these drugs can also dissolve beneficial clots or injure healthy tissue causing potentially fatal bleeding complications.

While a variety of interventional devices are available, including angioplasty, atherectomy, and laser ablation catheters, the use of such devices to remove obstructing deposits may leave behind a wound that heals by forming a scar. The scar itself may eventually become a serious obstruction in the blood vessel (a process known as restenosis). Also, diseased blood vessels being treated with interventional devices sometimes develop vasoconstriction (elastic recoil), a process by which spasms or abrupt reclosures of the vessel occur, thereby restricting the flow of blood and necessitating further intervention. Approximately 40% of treated patients require additional treatment for restenosis resulting from scar formation occurring over a relatively long period, typically 4 to 12 months, while approximately 1-in-20 patients require treatment for vasoconstriction, which typically occurs from 4 to 72 hours after the initial treatment.

The use of vibratory energy, typically in the ultrasonic range, has been proposed both to mechanically disrupt clots and to enhance the intravascular delivery of drugs to dissolve clots and inhibit restenosis. Vibrational energy may be delivered intravascularly using specialized catheters having a typically ultrasonically vibrating surface at or near their distal ends.

While highly promising, prior vibratory catheter designs have not always been able to provide the directions, modes, strengths, and other energy characteristics which are required or optimized for clot disruption or drug delivery. Specifically, prior vibratory catheters have not always been able to provide desired levels of mechanical disruption when the oscillating elements of the catheter are immersed in viscous fluid. This is especially true of catheters having smaller vibrational transducers which can reach areas in the vasculature or other body lumens unaccessible to catheters using larger transducers or vibrational generators located outside of the body. Furthermore, devices with external generators suffer from energy losses at all catheter bending points, resulting in variable and unpredictable amounts of vibrational energy at the catheter tip.

It would be desirable to provide improved devices, systems, and methods for treating vascular and other lumenal diseases, particularly stenotic diseases which occlude the coronary and other arteries. In particular, it would be desirable to provide novel vibratory catheter configurations using a plurality of vibratory oscillators capable of providing desired levels of mechanical disruption and/or fluid mixing. Such catheter configurations should be compatible with conventional catheter designs, such as angioplasty catheters, drug delivery catheters, perfusion catheters, and atherectomy catheters, but should also be useful as stand-alone devices intended to disrupt clot in blood vessels and perform other procedures in different body lumens. At least some of these objectives will be met by the catheter designs described and claimed hereinafter.

2. Description of the Background Art

Catheters having ultrasonic elements with the capability of delivering thrombolytic and other liquid agents are described in U.S. Pat. Nos. 5,362,309; 5,318,014; 5,315,998; 5,197,946; 5,380,273; 5,344,395; 5,342,292; 5,324,255; 5,269,297; 5,267,954; 4,808,153; 4,692,139; and 3,565,062; in WO 90/01300; and in Tachibana (1992) *JVIR* 3:299–303. See, in particular, FIGS. 6A and 6B of U.S. Pat. No. 5,197,946, which disclose a cantilevered transducer designed for non-bending actuation. A catheter system having a pair of spaced-apart balloons with a coiled piezoelectric strip therebetween is described in U.S. Pat. No. 5,279,546. Catheters having elongate ultrasonic transmission elements and inflatable cuffs are described in U.S. Pat. Nos. 5,397,301; 5,304,115; and 4,870,953. A tunneling catheter having a radiofrequency, laser, or ultrasonic active distal end disposed within an angioplasty catheter is described in EP 189 329. An atherectomy catheter having an ultrasonically enhanced blade disposed adjacent an asymmetrically mounted balloon is described in U.S. Pat. No. 5,085,662. Phonophoresis transducers disposed within porous, inflatable balloons are suggested in U.S. Pat. Nos. 5,286,254 and 5,282,785. A rigid ultrasonic probe intended for treating vascular plaque and having fluid delivery means is described in U.S. Pat. No. 3,433,226. An ultrasonic transmission wire intended for intravascular treatment is described in U.S. Pat. No. 5,163,421 and Rosenschein et al. (1990) *JACC* 15:711–717. Ultrasonic enhancement of systemic and localized drug delivery is described in U.S. Pat. Nos. 5,267,985; and 4,948,587; in WO 94/05361 and WO 91/19529; in JP 3-63041; and Yumita et al. (1990) *Jpn. J. Cancer Res.* 81:304–308. An electrosurgical angioplasty catheter having ultrasonic enhancement is described in U.S. Pat. No. 4,936,281. An infusion and drainage catheter having an ultrasonic cleaning mechanism is described in U.S. Pat. No. 4,698,058. Angioplasty balloon catheters having axial blade atherectomy, ultrasonic imaging, and rotary blade atherectomy devices at their distal ends are described in U.S. Pat. Nos. 5,053,044; 5,117,831; and 5,181,920, respectively. Ultrasonic imagery catheters having multiple transducers arranged in a phased array are described in U.S. Pat. No. 3,938,502 to Bom.

The present application is related to co-pending applications assigned to the assignee of the present application having the following Ser. Nos. 08/565,575; 08/566,740; 08/566,739; 08/708,589; and 08/867,007.

The full disclosures of each of the above listed U.S. patents and co-pending applications are hereby incorporated herein by reference.

SUMMARY OF THE INVENTION

According to the present invention, improved devices and methods are provided for the delivery of vibrational energy to body lumens, such as blood vessels. The devices are usually catheters useful for the primary or ancillary treatment of lumenal disorders, such as vascular occlusive diseases. Such treatment can be in the form of the delivery of vibrational energy for the primary disruption of clot or plaque at a stenosed region within the blood vessel. The treatment may also comprise the delivery of vibrational energy to enhance the intramural penetration or activity of drugs which are delivered to a diseased region of the body lumen. Further, the treatment may be for the direct degradation of vascular cells in the form of programmed cell death referred to in the literature as apoptosis. The disruption of stenotic material, the delivery of drugs, and cell disruption can be performed in combination with other primary treatments, such as angioplasty, atherectomy, laser ablation, stent delivery, and the like.

The present invention enhances the delivery of vibrational energy from a catheter by providing two or more oscillators or transducers on the catheter, usually near the distal end, wherein the oscillators each have one or more vibrational surfaces which interact or cooperate with one or more vibrational surfaces on at least one other oscillator to enhance, modify, or otherwise effect a unique vibratory output from the combination. The oscillators and their vibrational surfaces may be arranged in a variety of patterns and may be driven in a variety of phase relationships to achieve an almost unlimited number of potential vibratory outputs. Advantageously, multiple transducers can reduce the problem of catheter recoil since the transducers can be designed to "beat" against themselves, offsetting some of the vibrations to the catheter body.

In one embodiment of the present invention, the catheter of the present invention comprises a catheter body having a proximal end and a distal end. The catheter has a plurality of oscillators, where each of the oscillators has at least one vibrational surface and at least some of the vibrational surfaces are disposed to cooperatively input energy to a fluid therebetween. The oscillators may comprise sonic or ultrasonic transducers and the surfaces are usually vibrated in the sonic to low ultrasonic range with energy being transferred to the liquid environment surrounding the distal end of the catheter. The catheters may also have a lumen extending from the proximal end to a point near the oscillators, typically located near the distal end of the catheter body. The lumen may be used to inject and/or aspirate fluid to or from the catheter and may terminate in a distal opening or aperture disposed between at least two of the vibratory surfaces.

Figure 1A:
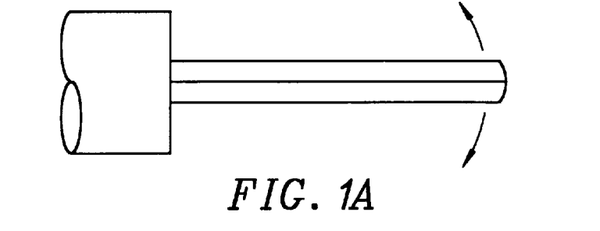
FIGS. 1A–1B depict bender-type and expanding-type oscillators for use with the present invention (it should be noted that the bending of the oscillators in the figures is exaggerated for purpose of explanation).
Figure 1B:
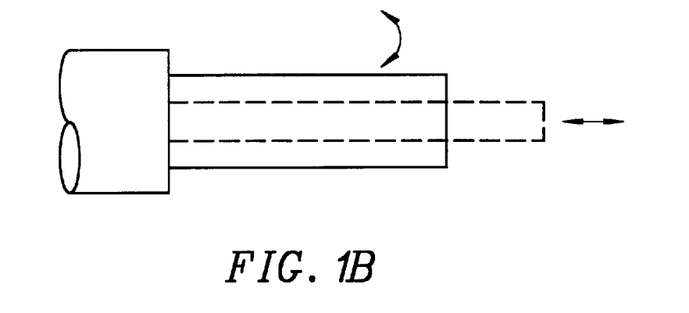

In one aspect of the present invention, the oscillators used with the catheter can provide a variety of different vibrational surface motions, such as a bending-type motion or an expanding-type motion. In a bending-type motion, at least one of the plurality of oscillators has a bending vibrational surface, with the oscillator arranged to vibrationally flex the surface about an axis within a plane of said oscillator (FIG. 1A). In an expanding-type motion, opposed vibrational surfaces on an oscillator typically reciprocate relative to each other as the oscillator expands and contracts (FIG. 1B). The bending or expanding of these oscillators may be achieved through the use of piezoelectric, magnetostrictive, or similar material which transduce energy such as electricity into mechanical motion. Optionally, resonant oscillators may also be used. These materials may be formed into various configurations, such as a piezoelectric tube or stack, or combined with other materials to achieve a desired motion from the oscillator. In one preferred embodiment, bimorph bending oscillators are used with the present invention.

Figure 1C:
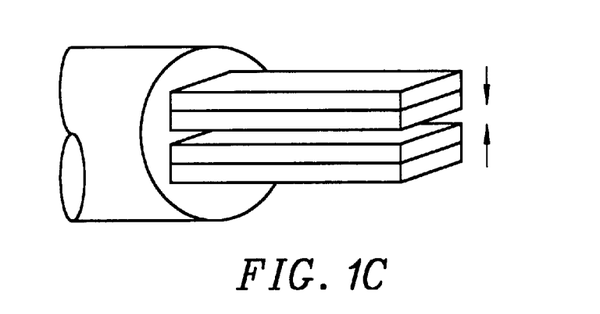
FIGS. 1C–1D show various configurations for positioning a plurality of oscillators on a catheter of the present invention.
Figure 1D:
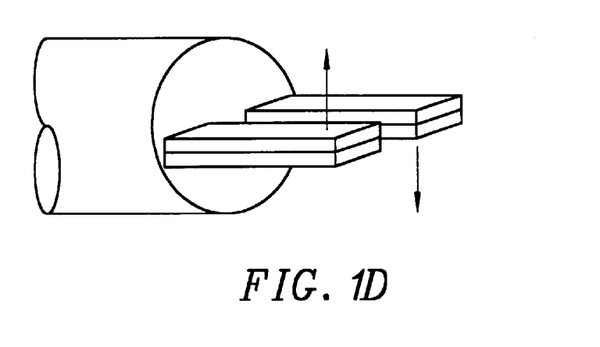

In another aspect of the present invention, energy transfer from a catheter may be enhanced by arranging vibrational surfaces of a plurality of oscillators in specific geometries or patterns. For example, with bending-type oscillators, the vibrational surfaces may be disposed in a pattern where the surfaces are generally opposed to one another along one of two possible orientations (FIGS. 1C and 1D), for compressive or shearing effects, respectively. The surfaces may be side-by-side, axially spaced apart, or symmetric about an axis of the catheter. Arranging the vibrational surfaces in a desired pattern allows the surfaces to work in conjunction to magnify the effectiveness of the oscillators. For bending oscillators, immersed in a fluid, coordinating the oscillators allows the translation of lateral oscillator motion into forward or outward movement of fluid. It may also increase the range of displacement between two vibrational surfaces.

In specific embodiments, the catheter of the present invention essentially has a fluid pump assembly located near the distal end of the catheter body. The fluid pump assembly typically comprises a plurality of oscillators having vibrational surfaces disposed relative each other such that the combined action of the vibrational surfaces acts to pump fluid. The use of oscillators advantageously simplifies catheter construction and allows the use of smaller vibrational sources.

According to the present invention, a method for intralumenal delivery of vibrational energy to a body lumen comprises the step of providing a catheter having a plurality of oscillators on a distal end of the catheter, where the oscillators each have at least one vibrational surface. The catheter is positioned adjacent a target site within the body lumen and the oscillators are energized to input vibrational energy into the target site or fluid. Energizing the oscillators vibrates the vibrational surfaces, which may be vibrated in-phase or out-of-phase with one another. The oscillators may be vibrated at a wide range of frequencies, typically from about 60 Hz to 100,000 Hz, usually from about 1000 Hz to 40,000 Hz. Oscillators vibrating between 1000 Hz to 40,000 Hz may generate a velocity gradient between about $10^4$ to $10^7$ per second. A therapeutic agent may be released at the target site when the oscillators are moving such that the energy from the catheter activates and/or enhances delivery of the agent.

In addition to the geometry or pattern of the oscillators, the effectiveness of the catheter may be further increased by coordinating the motion of the vibrational surfaces on the oscillators. The plurality of oscillators on the catheter may be driven at the same or different frequencies. When the oscillators are moving at the same frequency, a phase relationship exists between the vibrational surfaces on these oscillators. The vibrational surfaces on the oscillators may be moving in- or out-of-phase with at least one other surface. When the surfaces are 180 degrees out-of-phase, a maximum range of displacement can be achieved between two opposing vibrational surfaces. Other degrees of phase shift may be used to vary the type of vibratory output from the catheter. It is to be appreciated that the phase relationship between the oscillators will directly determine the nature of the acoustic output, ranging from longitudinal or lateral bursts of displaced intermediate fluid to the longitudinal or lateral movement of the fluid mass as a whole.

A further understanding of the nature and advantages of the invention may be realized by reference to the remaining portions of the specification and the drawings.

DESCRIPTION OF THE SPECIFIC EMBODIMENTS

I. General

The present invention provides apparatus and methods for the treatment of lumenal conditions, particularly for the treatment of diseases of the coronary and peripheral vasculature. Specific conditions include coronary and peripheral arterial disease and thrombosis. The apparatus and methods are useful for primary treatment of such diseases, where the purpose is to ablate, dissolve, or otherwise disrupt the clot, plaque, or other stenotic lesions which are responsible for the disease, or for the purpose of preventing the reoccurrence of these diseases. Apparatus according to the present invention operate by transferring vibratory energy into an environment surrounding the distal end of a catheter. Energy can be transferred directly into tissue, stenotic material, or other structures within the lumen or can be transferred into liquid material surrounding the catheter tip, as described in more detail below.

The terms "vibration" or "oscillation" as used in the application refer to a physical displacement of all or a portion of the vibrational surface on an oscillator. This displacement can be referred to directly as a physical movement of some portion of the device. Alternatively, when combined with frequency, physical movement may be described by the resultant pressure or acoustic intensity. When further combined with the surface area in motion, the physical movement may be described in terms of energy. The displacements are typically in the range of about 0.02 to 200 microns, usually being in the range from 5 to 20 microns, and may occur as a bending or reciprocating motion. Further, individual oscillators on a catheter of the present invention may be driven at the same or different frequencies. As discussed in detail below, oscillators moving at the same frequency may be phase shifted relative to one another to create a desired vibratory output from the catheter.

Figure 2A:
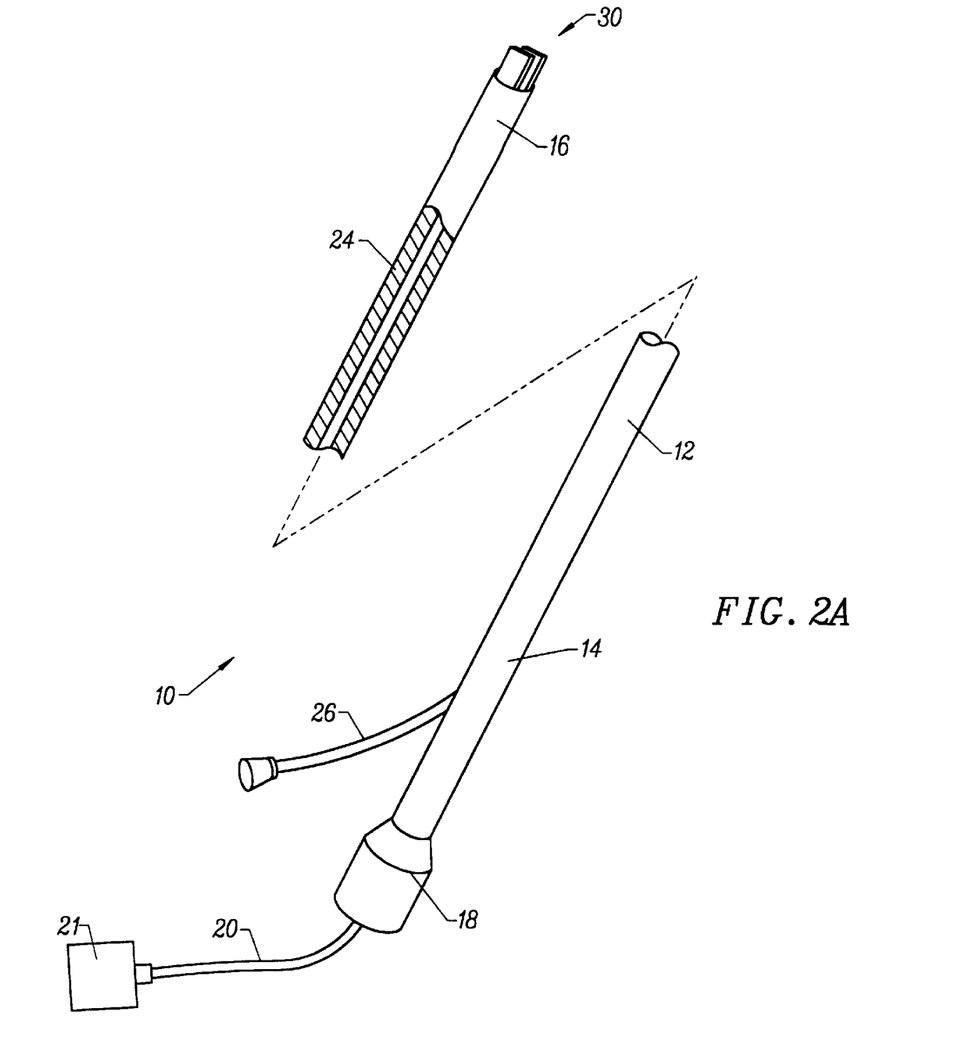
FIG. 2A is an partial cross-sectional view of a catheter constructed in accordance with the principles of the present invention, having a vibrational transducer projecting distally from a distal end thereof.
Figure 2B:
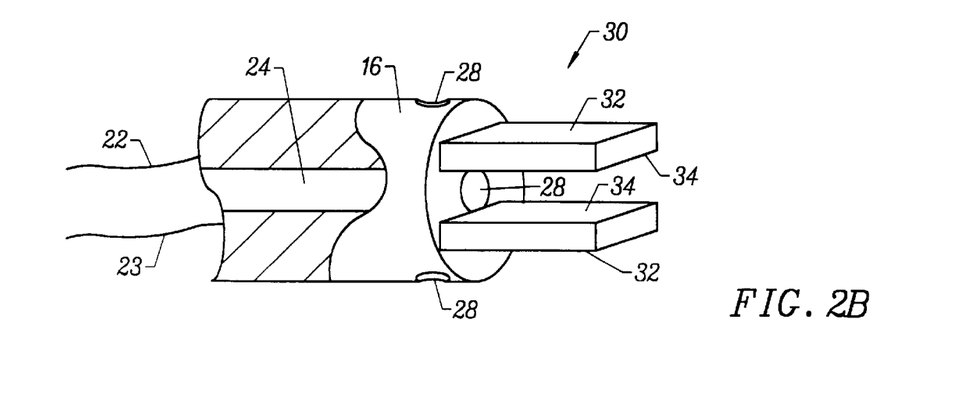
FIG. 2B is a detailed, partial cross-sectional view of the distal end of the catheter of FIG. 2A.

Referring to FIGS. 2A and 2B, a catheter 10 constructed according to the principles of the present invention having a vibrational transducer assembly 30 can be used for any of the purposes set forth above, e.g. to directly engage and transmit vibratory, usually ultrasonic, energy to mechanically disrupt stenotic material in a blood vessel and/or to generate active circulation and vortices in a liquid environment surrounding the distal tip of the catheter. The transducer assembly 30 may be designed to operate over a broad spectrum of frequencies including sonic and ultrasonic frequencies the transducer assembly 30 can be connected to an amplifier 21 in order to induce vibrations in the surfaces of the assembly 30.

II. Catheter Body catheter 10 of the present invention will comprise a catheter body 12 having a proximal end 14 and a distal end 16. A proximal hub 18 will be attached to the proximal end 14 of the catheter body 12. A connecting cable 20 enters the catheter 10 through the hub 18 and provides for external connection to wires 22 and 23 which provide power to vibrational transducer assembly 30. The catheter body 12 will have dimensions and physical characteristics selected for the particular use. For vascular applications, the length of the catheter body will typically be from 50 cm to 200 cm, usually being from 75 cm to 150 cm, and the diameter will be from 1 mm to 5 mm, usually being from 2 mm to 4 mm. The diameter of the catheter body 12 may vary over its length, and different portions of the length may be formed from different materials.

Conventional materials for the catheter body 12 include synthetic and natural polymers, usually being thermoplastics, such as nylon, polyurethane, polyethyleneterephthalate (PET), polyvinylchloride (PVC), polyethylene, and the like. The catheter body 12 may be composed of these conventional materials and optionally reinforced over all or a portion of its length. Such material may be conveniently extruded into tubular shapes useful for forming the catheter bodies of the present invention. Reinforcement materials may be introduced during the extrusion process or subsequent to extrusion by thermal processes, such as partial melting. Conventional reinforcement materials include wire and ribbon braids, wire meshes, wire coils, helical ribbons, and the like.

As shown in FIG. 2B, catheter body 12 may have a lumen 24 which extends through the length of the catheter body 12 and exits the catheter body near distal end 16. In particular embodiments, the lumen 24 exits the distal end 16 adjacent to the vibrational transducer assembly 30. In an exemplary embodiment, the catheter body 12 will comprise a single extrusion typically having more than one lumen 24 therethrough for providing guidewire access, drug infusion access, inflation medium access, or the like, plus a facility for electrical leads from the proximal end to the distal end. When employed with a guidewire for placement within the vasculature, the catheter body 12 may have an "over-the-wire" design or a "rapid exchange" design. In the former case, a guidewire lumen (not shown) will extend substantially through the entire length of the catheter body. In the latter case, the guidewire lumen will terminate in a proximal guidewire port located relatively near the distal end of the catheter body, usually within 50 cm, more usually within 30 cm, and often within 25 cm or less.

Often the catheter body 12 may include multiple, separate lumens for balloon inflation, delivering therapeutic agents, routing electrical wires for connection to the vibrational transducer assembly 30, or other purposes. Additionally, lumen 24 may exit the catheter body 12 in a plurality of infusion ports 28 near distal end 16 of the catheter body 12. These infusion ports 28 may be used for injection as well as suction of thrombolytic or body fluids from a target site.

III. Vibrational Transducer Assembly

As illustrated in FIGS. 2A and 2B, the vibrational transducer assembly 30 typically comprises two oscillators 32 located near the distal end 16 of the catheter body 12. Although not restricted in this manner, the oscillators 32 are usually anchored within the catheter body 12, typically near the distal end 16, more typically within 0 cm to 5 cm of the distal end 16, preferably within 0 cm to 1 cm of the distal end 16. As described in more detail below, the oscillators 32 may be arranged in pairs, in groups of three, in groups of four, or in higher numbers, typically being symmetrically arranged about the cross-section of the catheter body 12.

The oscillators 32 comprising the transducer assembly 30 each have one or more vibrational surfaces 34, where at least some of the vibrational surfaces 34 are disposed to cooperatively input energy to a liquid or structure near the assembly. The "interaction" or "cooperation" of the surfaces 34 may involve moving the vibrational surfaces on oscillators in a particular motion relative to one another, at a specific frequency relative to one another, or otherwise coordinating the surfaces on the oscillators to enhance, modify, or otherwise effect a unique vibratory output from the combination.

In a preferred embodiment of the present invention, each of the oscillators 32 has at least one vibrational surface 34 opposed or at least partially opposed to a vibrational surface 34 on another oscillator 32. This oscillator configuration allows the movement of vibrational surfaces to be coordinated which can maximize the vortices and/or velocity gradients in fluid or structure adjacent the vibrational transducer assembly 30. Having opposed or partially opposed vibrational surfaces 34 allows the assembly 30 to provide a variety of outputs. The opposing surfaces orientation may facilitate fluid pumping of liquid and create velocity gradients in fluid or structures near the distal tip of the catheter. A velocity gradient is the change of the velocity over a small spatial distance at a specific point in time. Velocity gradients created by the transducer 30 are typically in the range of about $10^3$ to $10^8$ per second, more preferably between about $10^4$ to $10^7$ per second. Opposed vibrational surfaces may also allow the transducer assembly 30 to physically grip and engage targeted material to chew or tear at the material. The engaging and disengaging of tissue may also increase the efficiency of thrombolytic agents by exposing untreated material and creating a mechanical disturbance of fluid near the transducers.

The vibrational transducer assembly 30 may comprise a variety of different types of oscillators 32, including piezoelectric, magnetostrictive, and the like. The transducers may further include known resonant drives for amplification of the displacement, energy, or both. The transducers may be located on the catheter typically at the distal end and may be disposed internally or externally on the catheter. Whatever type or types of oscillators are used, the transducer 30 will still rely on a coordinated or interacting motion of a plurality of oscillators to generate mechanical disruption and/or local velocity gradients in the liquid or structure surrounding the transducer.

Vibrational transducer assembly 30 may exhibit two types of vibrational waves: standing waves and travelling waves. The standing waves are large in amplitude and are typified by observable inertial nodes (i.e., loci along the longitudinal axis of the oscillator which remain nearly stationary during vibration at the resonant frequency), and inertial anti-nodes (i.e., loci which represent local maxima of vibrational motion). These vibrations are more observable in bending oscillator devices where the oscillators themselves may flex in configurations similar to the shapes depicted in FIGS. 5A–5B. Travelling waves are not easily observable, not having the nodal structure of standing waves, yet they are responsible for a majority of the energy flow for expanding-type or piston-type oscillators discussed below.

For treating coronary and peripheral arterial disease and thrombosis, the vibrational transducer assembly 30 provides a catheter 10 of the present invention with the ability to generate turbulence and optionally thermal energy to disrupt or lyse stenotic material in an associated blood vessel lumen. Turbulence and mechanical disruption created by the vibrational transducer assembly 30 will improve the effectiveness of thrombolytic or clot dissolving agents injected into the blood vessel lumen to facilitate unclogging of the blood vessel.

In particular, it is desirable to mechanically disrupt the clot or stenotic material in the presence of thrombolytic or clot dissolving agents so that the vibrational transducer 30 and the thrombolytic agents can more quickly remove the obstruction by peeling away treated material to expose further untreated stenotic material that has not been exposed to the thrombolytic agent. The catheter 10 of the present invention may be used to recirculate and vigorously agitate a small amount of thrombolytic agent introduced to a target site in the blood vessel lumen. In some respects, the transducer assembly 30 may be viewed as a fluid pumping assembly. Such vigorous mechanical disruption and recirculation near the target site is desirable to minimize the amount of thrombolytic agent used in the procedure. Injecting excessive amounts of a thrombolytic agent into a patient's vascular system is not cost efficient and may cause undesirable dissolution of beneficial clots which may result in potentially fatal bleeding complications.

A. Bending-type Oscillators

Referring now to FIGS. 3A–3D, in a preferred embodiment of the present invention, catheter body 12 has a pair of bending oscillators 40 coupled to the distal end 16 of the catheter body. The bending oscillators 40 in FIGS. 3A–3D depict motion of the oscillators in an unloaded environment (i.e. in air or vacuum). The frequency of operation of the bending oscillator 40 will typically be in the range from 1000 Hz to 100,000 Hz, preferably from 1,000 Hz to 40,000 Hz, and more preferably from 2,000 Hz to 30,000 Hz. The vibrational amplitude will typically be in the range from 150 μm to 500 μm, when the system is unloaded. When the catheter 10 is present in its normal lumenal environment, i.e. surrounded by a natural body fluid, such as blood and/or by an introduced fluid, such as saline optionally carrying a drug, the vibrational amplitude will usually be damped to the range from 0.02 μm to 200 μm, more usually from 5 μm to 20 μm.

1. Material

The bending oscillator 40 preferably comprises a piezoelectric material which can be electrically excited to expand or contract. Typical piezoelectric material, under the influence of an electric field, either expands or contracts in the axis of the electric field, depending on the polarity of the field, while the material in axes perpendicular to the electric field reacts in an opposite manner. In simple terms, the volume of the piezoelectric material remains almost constant while expanding in one direction but shrinking in another. The bending oscillators 40 of the present invention may use such piezoelectric material in a variety of different configurations.

Figure 3A:
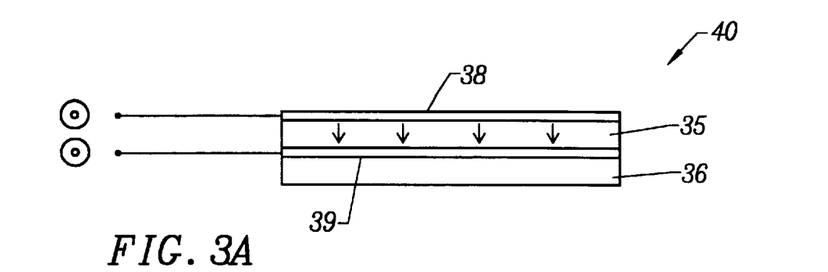
FIGS. 3A–3D show various configurations of a bending oscillator using a piezoelectric material.
Figure 3B:
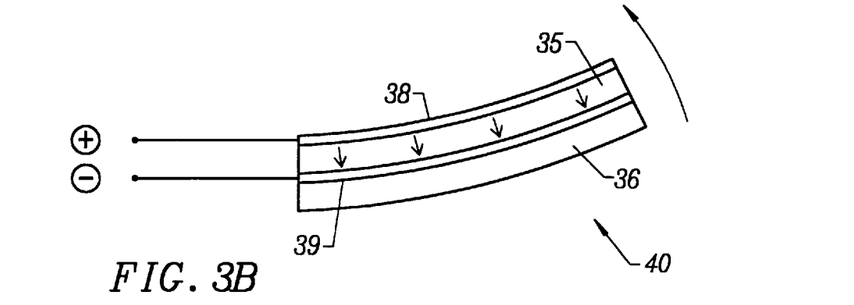

In a bimorph configuration, the bending oscillator 40 may use a single piezoelectric layer 35 laminated to an inert metallic strip 36 (FIG. 3A). With the application of an electric field across the piezoelectric layer 35 through electrodes 38 and 39, the length of the layer 35 will contract or expand depending on the polarity of the field. The metallic strip does not change its length, and consequently, the structure bends as shown in FIG. 3B.

Figure 3C:
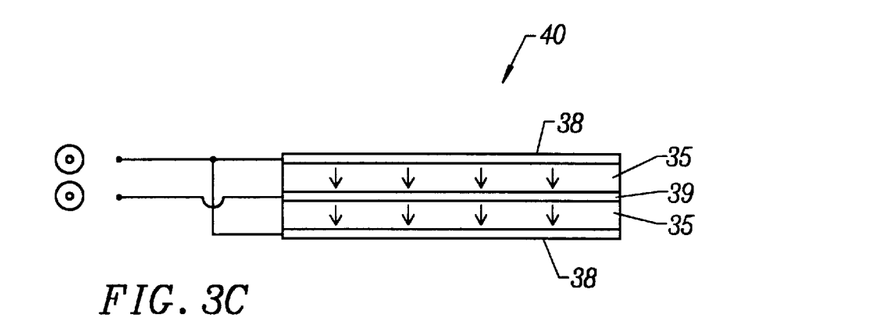
Figure 3D:
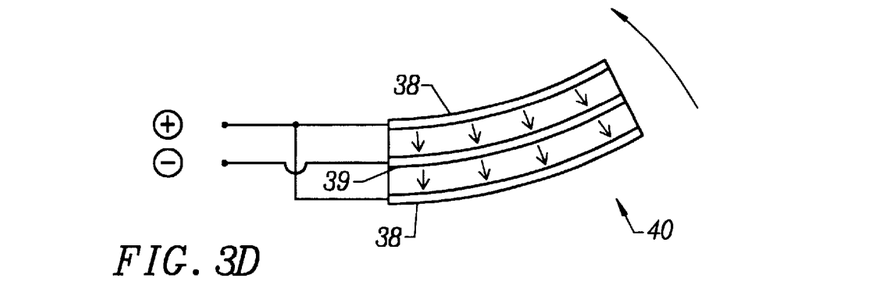

In a bimorph configuration of FIG. 3C, two piezoelectric layers 35 are laminated together with the polarization in the same direction and with the electrodes 38 and 39 wired with opposite polarities such that when a single voltage is applied, the length of one piezoelectric element expands while the length of the other element contracts. When one expands and the other contracts, the bimorph bends towards the direction of the element which contracts (FIG. 3D). The bimorph deflects into a bowed shape if it is relatively long and narrow or a cupped shape if it is both long and wide. The amount of deflection of the bimorph depends upon the voltage applied, within limits, and the thickness and lengths of the laminated components. As discussed below, when the voltage is oscillated, the shape of the bimorph also oscillates, and can be oscillated at a relatively high frequency.

Alternatively, a bending oscillator 40 may be configured as a unilaminar structure having an internally biased material (compressively stressed) such as those commercially available from Aura Ceramics, Inc., Minneapolis, Minn. Such structures are particularly convenient for use in the catheters of the present invention since they are compact, reliable, and provide relatively large displacements. Further details on the unilaminar structure and other suitable bending oscillators may be found in commonly assigned, copending application Ser. No. 08/867,007, filed Jun. 2, 1997, the complete disclosure of which has been previously incorporated herein by reference.

Figure 3E:
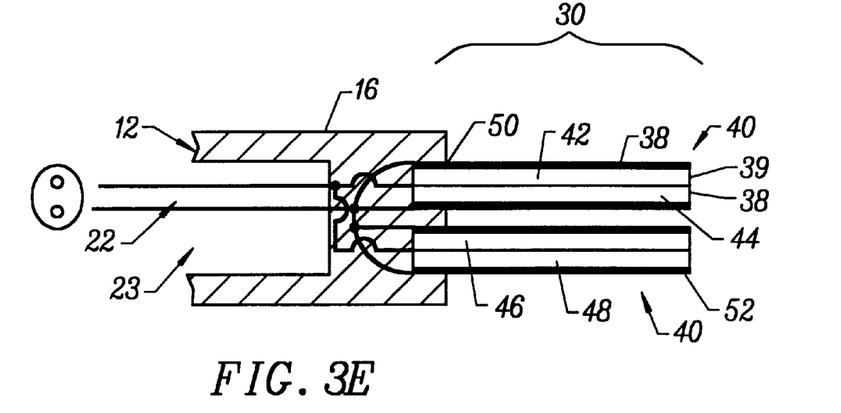
FIGS. 3E–3G illustrate a transducer configuration which may be utilized in catheters of the present invention under three electric field configurations.

Referring to FIG. 3E, one method of wiring a pair of bending oscillators 40 is shown. As illustrated in the figure, the outer electrodes 38 of the two piezoelectric layers 42 and 44 are wired together, typically the ground lead, while the common inner electrodes 39 of the two active layers share a common lead, typically the "hot" lead. This first bimorph comprising layers 42 and 44 is hence wired (by way of example) parallel to the second bimorph comprising piezoelectric layers 46 and 48.

The bending oscillator 40 of FIG. 3E is a bimorph oscillator in the form of a plate having a proximal end 50 and a distal end 52. The plate typically has a length in the range from about 2 mm to 12 mm, preferably from 4 mm to 8 mm, a width in the range from 1 mm to 4 mm, preferably from 2 mm to 3 mm, and a thickness (extending across the laminate of two layers 42 and 44) in the range from 0.05 mm to 1 mm, preferably from 0.1 mm to 0.4 mm. The laminates will flex or bend as depicted in FIGS. 3F and 3G when electrodes 38 and 39 are energized with either of the two possible polarities.

2. Bending Oscillator Motion

Figure 3F:
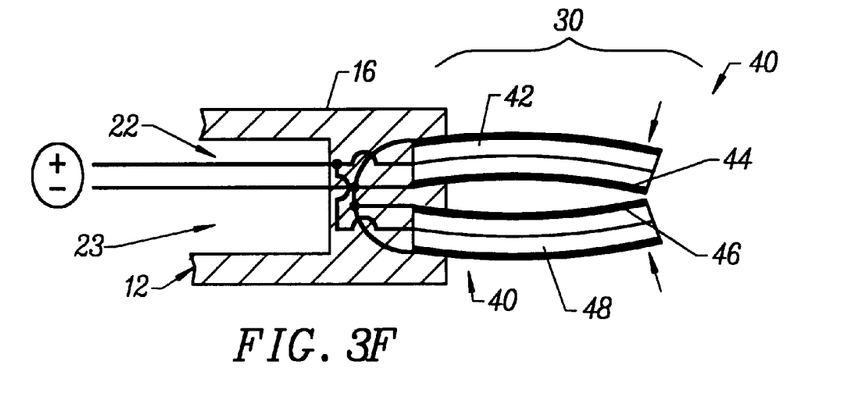
Figure 3G:
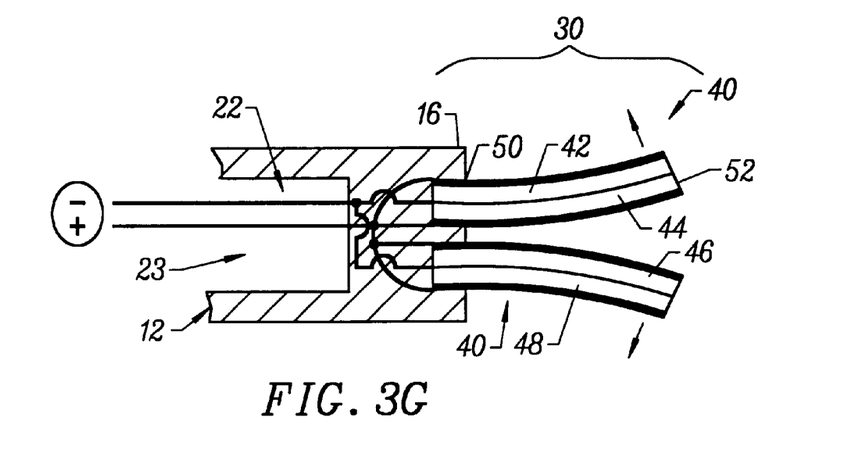

The motion of oscillators 40 is more clearly illustrated in FIGS. 3F and 3G. The alternating driving current will typically have a current in the range from about 0.01 mA to 10 mA, a voltage in the range from about 10 volts to 200 volts, and a frequency in the range from 60 Hz to 100000 Hz, usually from 2000 Hz to 30000 Hz.

Figure 4A:
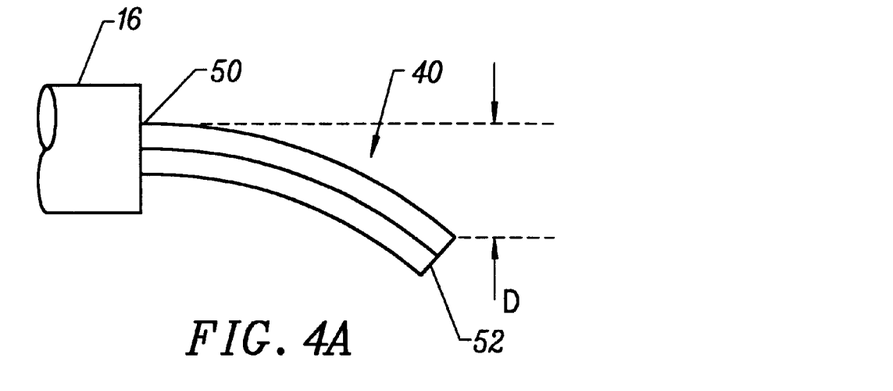
FIGS. 4A–4C depict the types of bending motion associated with a single bending oscillator in various mediums.
Figure 4B:
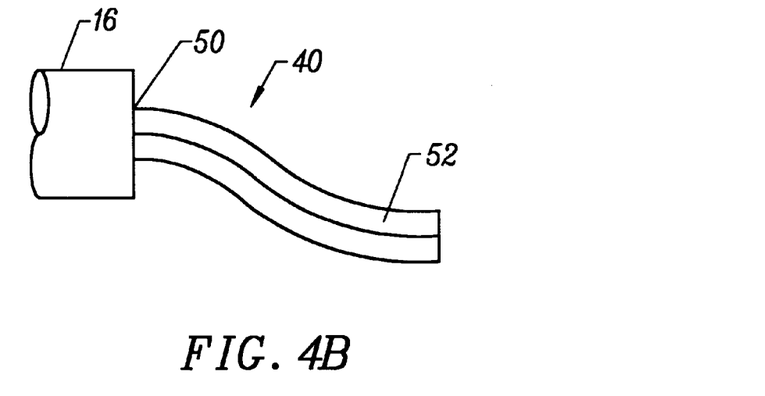

The motion of a bimorph bending oscillator 40 varies depending upon the medium in which the oscillator is immersed. Referring to FIG. 4A, bending oscillators 40 have been observed to oscillate in a fashion akin to a distal tip deflection of a cantilever beam while in an air or vacuum environment. The distal ends 52 of bending oscillators 40 have been observed to move over 250 microns in a resonance condition. In a viscous medium, however, movement of oscillator 40 is complex and characterized by resistance bending due to viscous damping as depicted by FIG. 4B. In a vacuum or air medium, the mass of the catheter body 12 compared to the mass of the bending oscillator 40 will cause the oscillator to experience more displacement at the distal tip 52 of the oscillator than at the distal tip 16 of the catheter. In a fluid environment such as the human blood field, viscous drag at the distal tip 52 will refer some level of vibrations back to the catheter distal tip 16. When bending oscillator 40 is actuated, the distal end 52 as shown in FIG. 3G and FIG. 4A will show reduced displacement. The portion of oscillator 40 between these ends 50 and 52, however, will still likely be displaced, possibly in a sinusoidal motion.

Figure 4C:
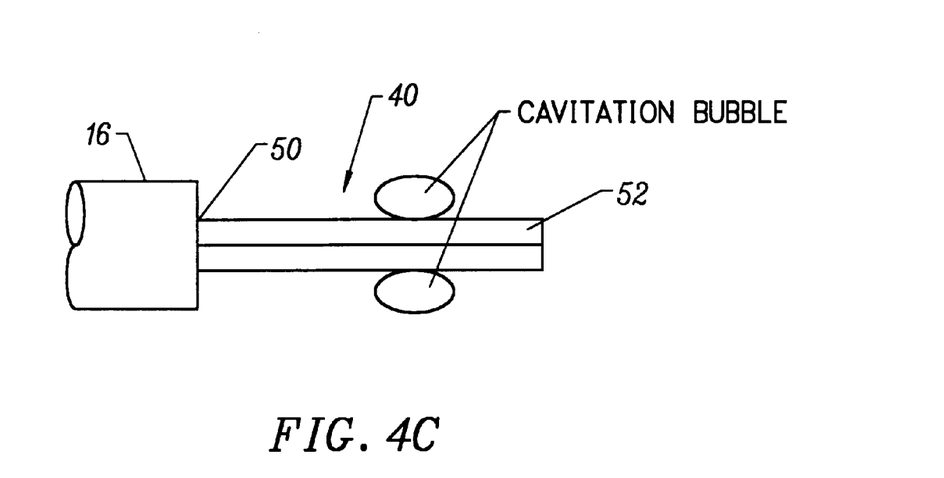

Depending on the oscillating current driving the bending oscillator 40, cavitation or the generation of small gas bubbles may be observed (as depicted in FIG. 4C) along portions of the length of the oscillator 40 due to the vibrational motion of oscillator. Cavitation facilitates the mechanical disruption of stenotic or obstructing material M and can also increase fluid mixing due to the aspirated condition of the fluids. The erratic motion of gas bubbles in such a fluid environment can also facilitate ultrasound imaging. It is hoped that the wide distribution of bubbles and microstreaming, perhaps in coordination with thrombolytic agents, can stimulate fluid mixing and further possibly remove stenotic material from a body lumen.

3. Coordination and Phase Relationship

Due in part to the constrained motion of the oscillator 32 in viscous mediums such as blood or saline, it is desirable that vibrational transducer 30 comprises a plurality of bending oscillators 32 operating in conjunction to maximize and the transmission of vibratory energy and to minimize referred vibrations to the catheter body 12. The various waveforms created by one oscillator 32 may be used advantageously in conjunction with another oscillator 32 to create or induce a variety of different fluid injection motions or vibrational outputs. As discussed below, by synchronizing the motion of opposing oscillators 32, the vibrational output from the transducer 30 can also be amplified due to cooperative motion of the oscillators 32.

Figure 5A:
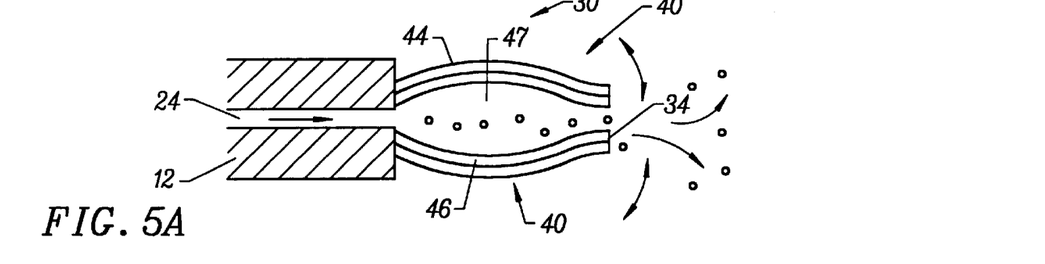
FIGS. 5A–5D show various configurations of a pair of bending oscillators.
Figure 5B:
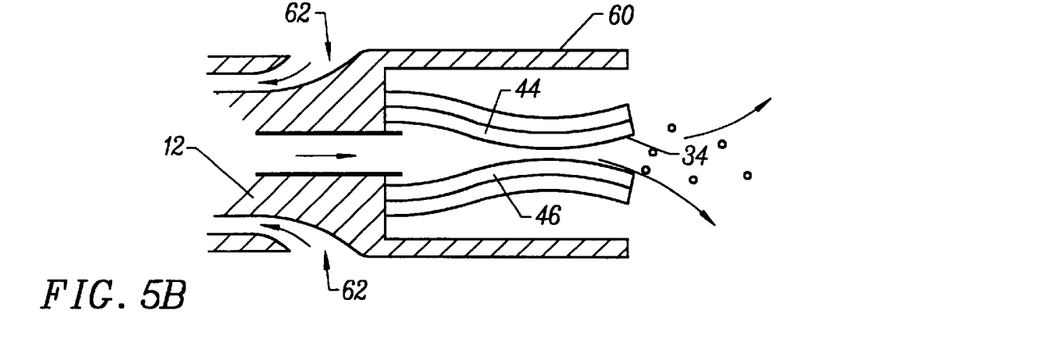

For example, as shown in FIGS. 5A and 5B, the bending oscillators 40 are positioned adjacent one another so that the vibrational surfaces on the inner, active layers 44 and 46 are opposed to one another and may interact to provide fluid propulsion and aspiration. Although it is not necessary that the vibrational surfaces be directly opposed to one another, the greater the overlap, the greater the amplification of fluid velocity gradients. On the outward swing or rarefaction (FIG. 5A), the oscillators 40 will draw fluid into the space 47 between the plates. On the inward swing or compression (FIG. 5B), the pair of oscillators 40 will forcefully expel any fluid entrapped between the plates. In this manner, not only do the oscillators 40 provide vibratory energy, but the oscillators 40 also act as a fluid pump. The lateral motion of the oscillators 40 is converted into forward directed fluid propulsion and vibratory energy. The motion of the oscillators 40 will also likely result in the generation and expulsion of cavitation bubbles into the medium and establish vigorous fluid microstreaming.

Optimal fluid pumping by the oscillators 40 requires phase coordination of oscillators moving at the same frequency. A pair of bending oscillators 40 having vibrational surfaces 34 on the inner, active layer 44 and 46 may oscillate 180 degrees out of phase in a sinusoidal motion to create a fluid pumping motion with the bending oscillators 40. In one embodiment, a pair of bending oscillators 40 moving 180 degrees out-of-phase, having an 8 square mm cross-sectional area, 12 micron spacing between vibrational surfaces 34, a combined stroke of ±2 microns, and an operating frequency of 3000 Hz, creates an average ejection velocity of approximately 1.6 m/s, which is roughly twice the natural flow rate of blood.

Figure 5C:
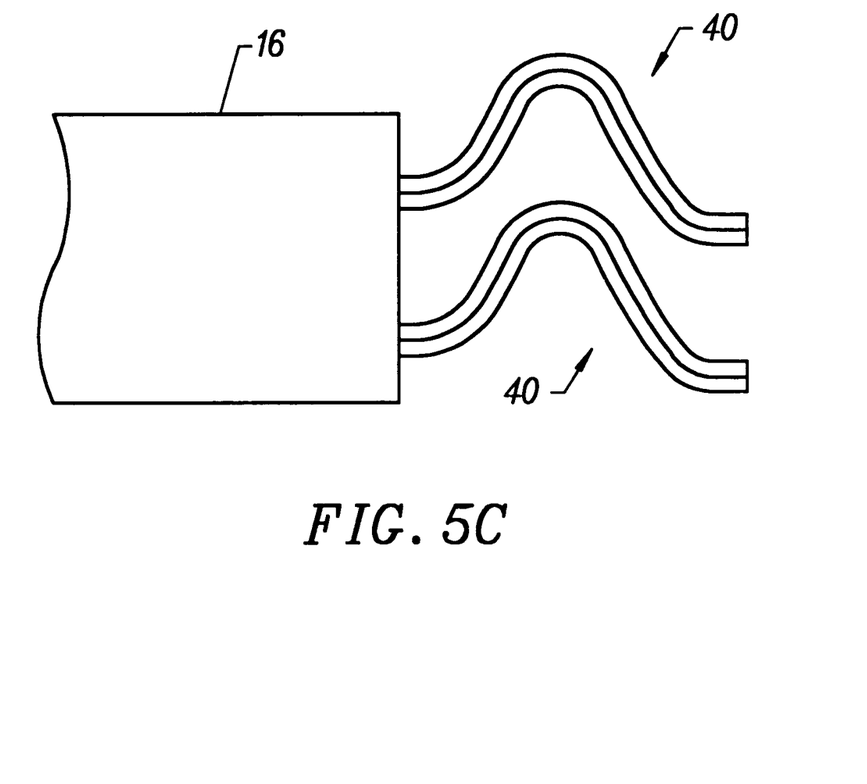
Figure 5D:
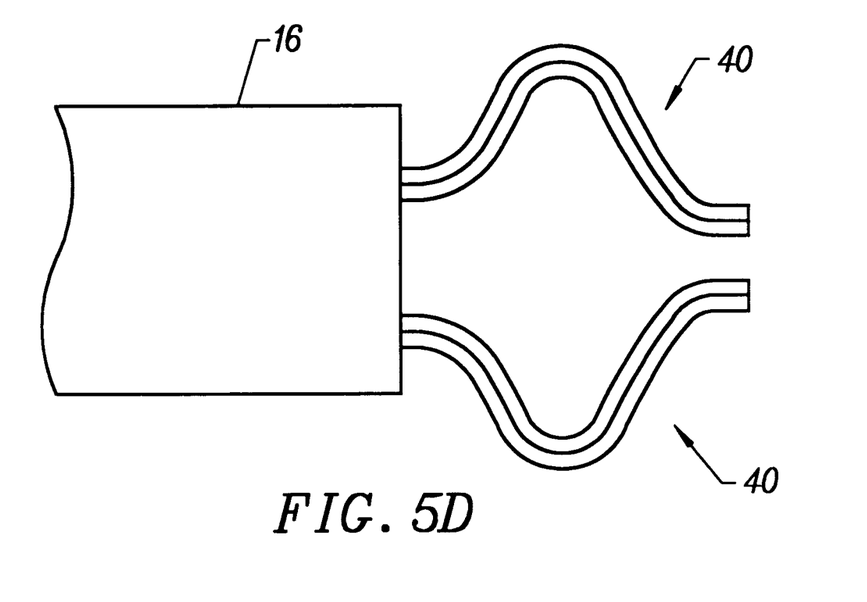

The vibrational output of the oscillators 40, however, is not confined to the output described above. The phase relationship between the preferably sinusoidal waveforms formed by the oscillators 40 may be adjusted to produce other particular outputs and oscillator configurations, as illustrated in FIGS. 5C–5D. FIG. 5C illustrates a pair of oscillators 40 moving in-phase to create a flipper-type motion. Further, the installment of multiple oscillators in parallel may improve the large amplitude resonance operation (closer to the air or vacuum environment) by overcoming to some extent the viscous drag on the leaflets of the oscillators. FIG. 5D illustrates a pair of oscillators 40 moving 90 degrees out of phase to vary the type of vibratory output from the catheter 10.

Further, the term coordination is not restricted to simply vibrational oscillators moving to set frequencies or movements. The term includes oscillators which operate their vibrational surfaces in some other manner with another oscillator's vibrational surface to input vibrational energy. In particular, coordination may be defined as two oscillators oriented to focus and transmit vibrational energy to fluid therebetween. Hence the output of the oscillators is combined together to increase the amount of mechanical disturbance.

The ejection velocity and turbulence of fluids passing between these bending oscillators 40, may be enhanced by the introduction of the fluid from a lumen such as injection lumen 24 exiting between the bending oscillators 40. The introduced fluid may comprise previously sonicated liquids to promote cavitation levels or thrombolytic agents to promote lysis of clots by active circulation and vortices generated by the oscillators. The ejection and active circulation of fluid from the catheter body 12, depicted in FIG. 5A, may be enhanced by enclosing the bending oscillators 40 at the distal end 16 of the catheter body with catheter wall extension 60. The catheter body 12 as depicted in FIG. 5B, may also have evacuation ports 62 located near the distal tip of the catheter body 12 to remove lysed cells, spent thrombolytic agents, or debris fragments from the target site within the body lumen.

Figure 6A:
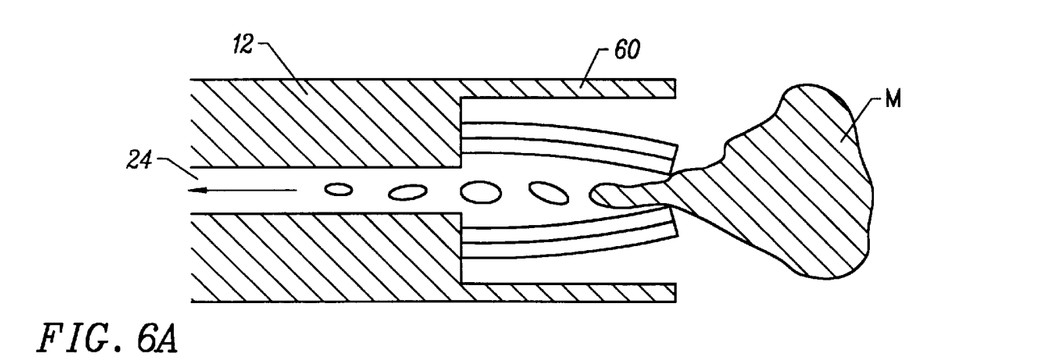
FIGS. 6A–6B show cross-sectional views of alternate embodiments of the distal tip of the catheter of FIG. 2A.
Figure 6B:
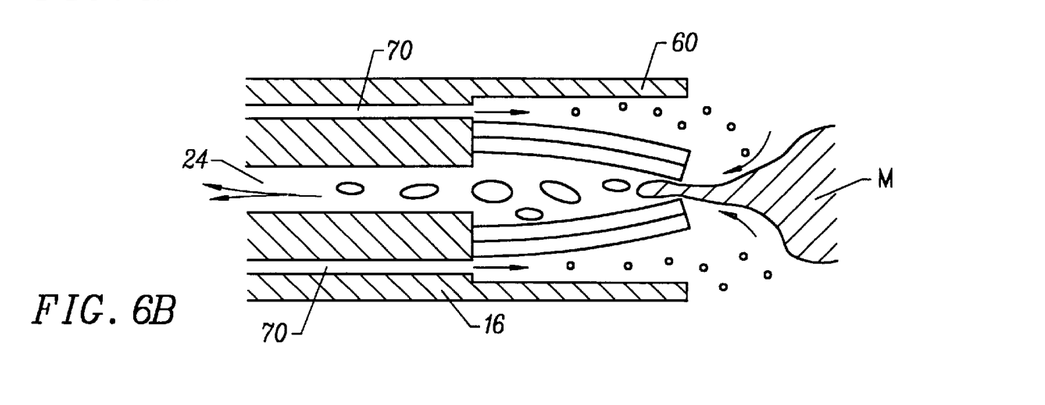
Figure 7:
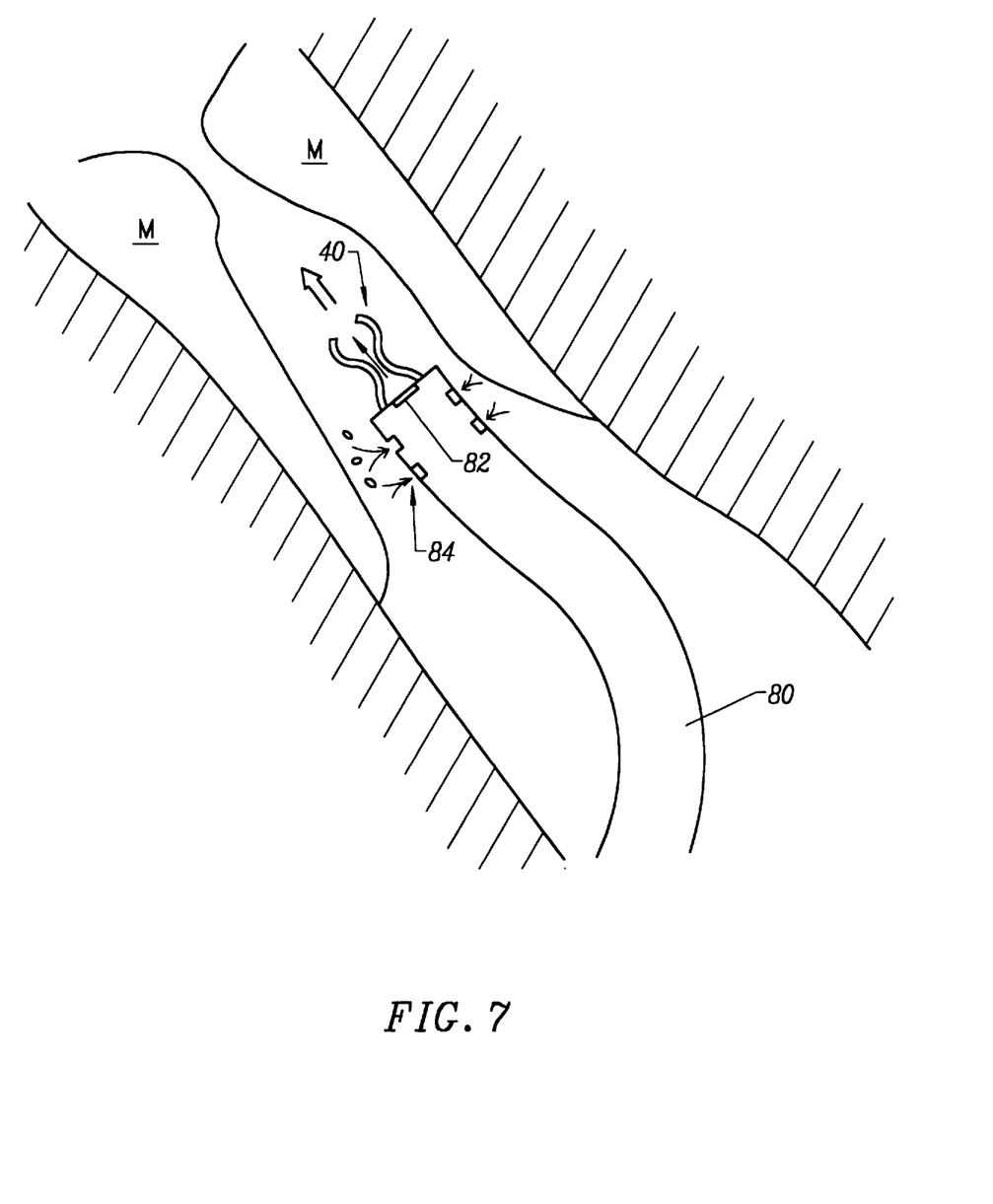
FIG. 7 shows an alternate embodiment of the catheter of the present invention in a body lumen engaging stenotic material.

In an alternate embodiment of the present catheter using bending oscillators 40, the lumen 24 may be used to evacuate rather than eject fluid from the distal end 16 of the catheter body 12. As the catheter body 12 is moved through the body lumen, a vacuum force is applied by the catheter near the target site to bring stenotic or obstructing material M into contact with the bending oscillators 40. The bending oscillators 40 are activated to chew the obstructing material M into fragments which can be evacuated from the body lumen or otherwise dispersed through the vacuum force applied by lumen 24. Referring to FIG. 6A showing a still further embodiment of the catheter body 12, a plurality of injection lumens 70 may be positioned near the distal tip 16 as depicted in FIG. 6B, to eject saline or thrombolytic agents. Such agents exiting the catheter distal tip 16 in an exited state on the outside of the bending oscillators 40 may be pulled back or directed into the area near or between the oscillators 40 to facilitate fragmentation of obstructing material M. The suctioning of fluid minimizes dissipation or dispersal of thrombolytic agents or saline away from the target site. Simultaneous fluid injection and fluid suctioning is also illustrated in FIG. 7. Catheter 80 having injection lumen 82 and fluid suctioning lumens 84 engages stenotic material M to increase the inner diameter of the body lumen. Energizing the bending oscillators 40 circulates fluids such as thrombolytic agents exiting the lumen 82.

B. Other Types of Oscillators

Figure 8A:
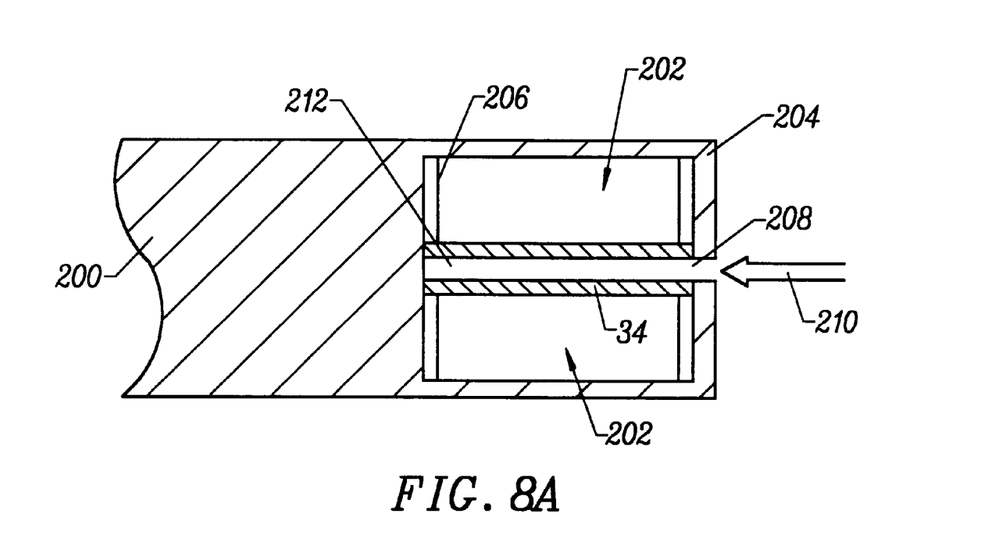
FIGS. 8A–8B are cross-sectional views of the distal end of another catheter constructed in accordance with the principles of the present invention, having a pair of piston or expanding type oscillators.
Figure 8B:
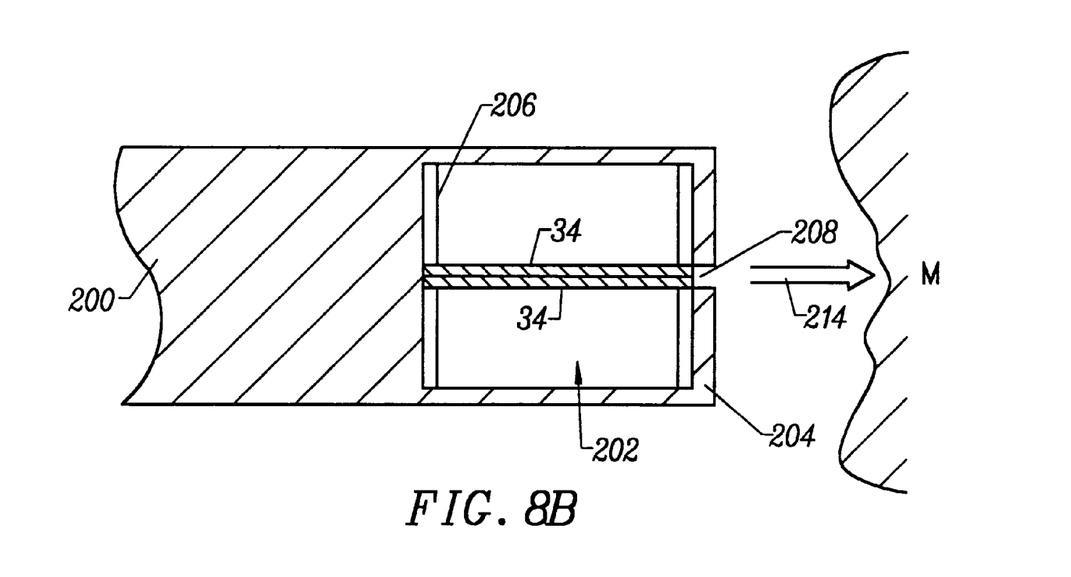

Although the embodiments of the catheter of the present invention described thus far use bending oscillators 40 to create active circulation and vortices near the target area of a body lumen, other types of oscillators such as expanding or piston-type oscillators may also be used to disrupt obstructions within the body lumen or promote fluid mixing. As shown in FIGS. 8A and 8B, the catheter 200 has a pair of piston-type oscillators 202 disposed near the distal end 204 of the catheter. The piston oscillators 202 have active layers 206 which expand to move vibrational surface 216 towards a second vibration surface 216 on an opposing piston oscillator 202 as shown in FIG. 8A. The vibrational surfaces 216 are spaced apart from one another and fluid is drawn into the catheter through port 208 as indicated by arrow 210. When the vibrational surfaces 216 are brought together, fluid is ejected from the space 212, through port 208 as indicated by arrow 214. The repeated expansion and contraction of active layer 206 on oscillator 202 moves vibrational surface 216 to cause suction and injection of fluid from the distal tip of the catheter 200.

Figure 9:
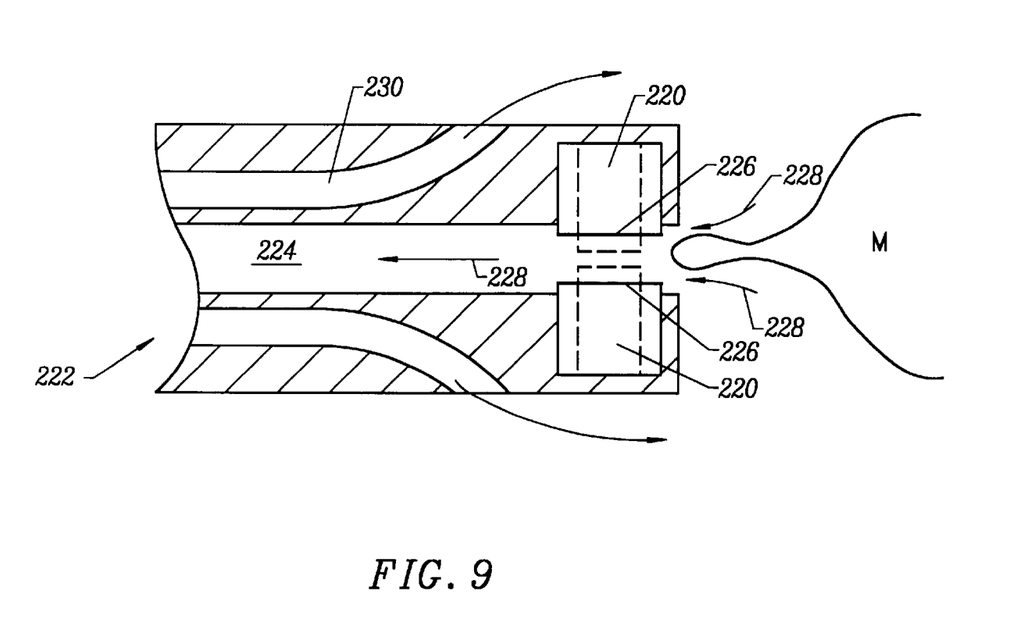
FIG. 9 shows a further embodiment of a catheter of the present invention using expanding type oscillators.

Referring to FIG. 9, the expanding-type oscillators 220 on catheter 222 may be used to create local velocity gradients and also to engage and chew material which enters the lumen 224. The oscillators 220 may expand, as shown by the dotted lines, to decrease the distance between vibrational surfaces 226 on oscillators 220. The motion of surfaces 226 towards each other can eject fluid trapped there between. With lumen 224 suctioning fluid and material into the catheter 222, as noted by arrows 228, the oscillators 220 may be able to chew or flatten material brought between the moving surfaces 226. Optionally, the catheter 222 may also have a fluid lumen 230 for injecting additional fluid or thrombolytic agent into the environment surrounding the catheter 222, either to further promote fluid mixing or removal of stenotic material.

Figure 10:
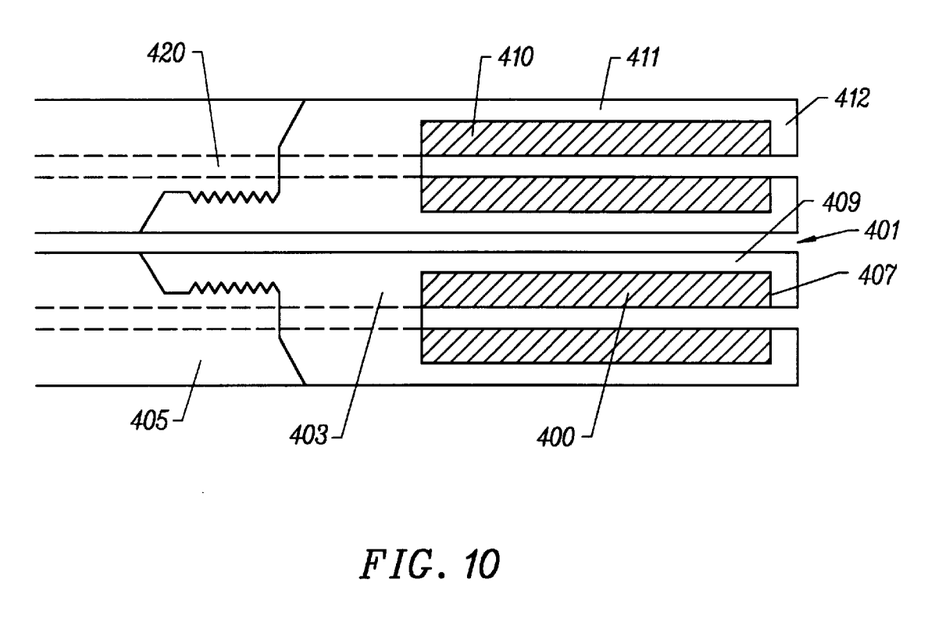
FIG. 10 depicts a further embodiment of a catheter according to the present invention.

A further utilization of multiple oscillators is depicted in FIG. 10, wherein two co-linear piezoelectric cylinders are utilized. Inner piezoelectric cylinder 400 has its primary mode of oscillation parallel to the longitudinal axis of the catheter, and is mounted between head mass 402, tail mass 403, and spring element 401, in a spring-mass configuration as recited in U.S. patent Ser. No. 5,620,479 issued Apr. 15, 1997, the full disclosure of which is incorporated herein by reference. Note that the spring element has a central lumen 404 extending from the distal tip of the catheter body for the purpose of passing a guide wire or expelling or evacuating fluids. Outer piezoelectric cylinder 410 is also mounted in the spring mass configuration between the head mass 412 and common base 403 with spring element 411. In the figure, the outer spring element also comprises the exterior wall of the catheter. The region between the two piezoelectric cylinders may be irrigated from lumens 420.

It is anticipated that the two cylinders will be designed for an equivalent mass and frequency, such that the net "kickback" to the catheter will be minimal when the two oscillators are driven 180 degrees out of phase. While the mechanical displacements of each of the head masses by themselves may be sufficient for clot lysis or drug delivery, it is expected that the velocity gradients produced around the annulus between the two head masses might produce an enhanced effect.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising:
   a catheter body having a proximal end, a distal end, and a longitudinal axis;
   at least two bending oscillators coupled to a distal end of the catheter body, wherein each of said oscillators has at least one vibrational surface disposed to cooperatively input energy laterally inwardly to a an interior volume therebetween.

2. A catheter as in claim 1 wherein the oscillators are adapted to vibrate the vibrational surfaces at ultrasonic frequencies.

3. A catheter as in claim 1 wherein said vibrational surfaces of each of said at least two oscillators are disposed in a pattern wherein the surfaces are generally parallel to a longitudinal axis of the catheter.

4. A catheter as in claim 1 wherein said plurality of vibrational surfaces are disposed in a pattern wherein the surfaces are generally symmetric about a longitudinal axis of the catheter.

5. A catheter as in claim 1 wherein said plurality of oscillators have vibrational surfaces opposed to one another along a longitudinal axis of said catheter.

6. A catheter as in claim 1, wherein said oscillators comprise at least one active layer which oscillates axially and transversely when energized and at least one opposed layer which constrains or oscillates non-synchronously relative to the active layer, wherein the relative axial and transverse displacement of the active and opposed layers causes transverse flexing of the oscillator.

7. A catheter as in claim 6, wherein the active layer comprises a piezoelectric material.

8. A catheter as in claim 1 wherein each of the plurality of vibrational surfaces are located within 1.0 μm.

9. A catheter as in claim 8, wherein each of the plurality of vibrational surfaces are located within 10 μm to 100 μm.

10. A catheter as in claim 1, wherein the oscillators project distally from the distal end of the catheter body.

11. A catheter as in claim 1 wherein the catheter body has a lumen extending from the proximal end to a point near the oscillators.

12. A catheter as in claim 11, wherein said lumen has a distal end between the vibratory surfaces.

13. A catheter as in claim 1 further comprising a fluid injection lumen and a fluid suction lumen, said lumens having orifices located near the distal end of the catheter body.

14. A method for intraluminal delivery of vibrational energy to a body lumen comprising the steps of:
   providing a catheter having at least two bending oscillators on a distal end of the catheter, said oscillators each having a vibrational surface;
   positioning said catheter adjacent a target site within the patient; and
   energizing said plurality of oscillators to cooperatively vibrate at least two vibrational surfaces to input energy laterally and inwardly into the target site or fluid.

15. A method of claim 14 wherein the energizing step comprises vibrating said vibrational surfaces out of phase.

16. A method as in claim 14, wherein said vibrational surfaces vibrate at a frequency in the range from 1000 Hz to 40000 Hz.

17. A method as in claim 14, further comprising releasing a therapeutic agent at the target site.

18. A method as in claim 17 wherein the agent is released via a lumen in the catheter.

19. A method as in claim 17, wherein the therapeutic agent is released prior to energizing the plurality of oscillators.

20. A method as in claim 17, wherein the therapeutic agent is released while energizing the oscillators.

* * * * *